United States Patent [19]

Simon

[11] 4,425,908

[45] Jan. 17, 1984

[54] BLOOD CLOT FILTER

[75] Inventor: Morris Simon, Boston, Mass.

[73] Assignee: Beth Israel Hospital, Boston, Mass.

[21] Appl. No.: 314,005

[22] Filed: Oct. 22, 1981

[51] Int. Cl.³ .................. A61M 29/00; A61B 19/00
[52] U.S. Cl. .............................. 128/1 R; 128/303 R; 128/325; 128/345
[58] Field of Search .................. 128/1 R, 214 R, 243, 128/341, 325, 345; 210/335, 448, 463

[56] References Cited

U.S. PATENT DOCUMENTS

| | | | |
|---|---|---|---|
| 3,137,298 | 6/1964 | Glassman | 128/328 |
| 3,334,629 | 8/1967 | Cohn | 128/325 |
| 3,540,431 | 11/1970 | Mobin-Uddin | 128/214 R X |
| 3,868,956 | 3/1975 | Alfidi et al. | 128/1 R X |
| 3,952,747 | 4/1976 | Kimmell | 128/1 R X |
| 4,274,408 | 6/1981 | Nimrod | 128/214.4 |

Primary Examiner—Dalton L. Truluck

[57] ABSTRACT

A blood clot filter is inwardly radially collapsible into a collapsed configuration for insertion into a vein, and upon insertion automatically radially expands into a predetermined functional form which is in contact with the inner wall of the vein. In the expanded configuration, the filter comprises a plurality of wires in the form of overlapping loops, with portions of the loops contacting the inner wall of the vein, providing a filter basket at the leading end of the filter; at the trailing end the wires have circumferentially spaced leg portions whose free ends contact the inner wall of the vein. The filter wires are composed of a material having a first, relatively pliable low-temperature condition and a second, relatively rigid high-temperature condition. A guide wire feeder device introduces the filter in its collapsed configuration into the blood vessel of a patient through a standard angiographic catheter. Upon emerging from the catheter, the filter responds to the ambient temperature and assumes its functional form.

9 Claims, 13 Drawing Figures

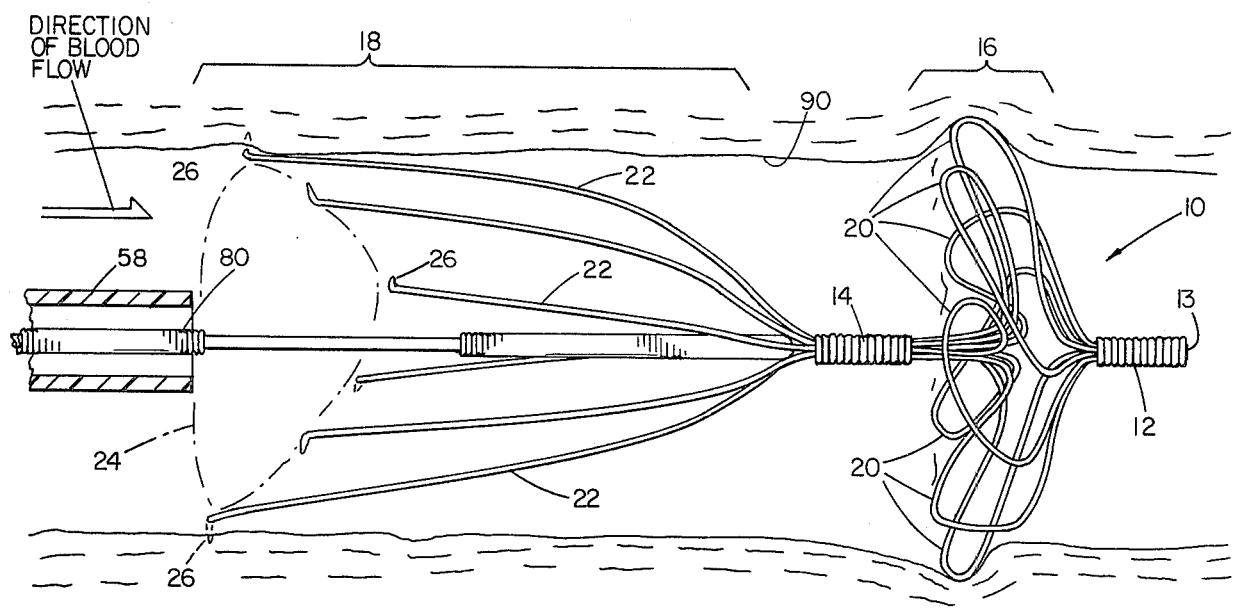
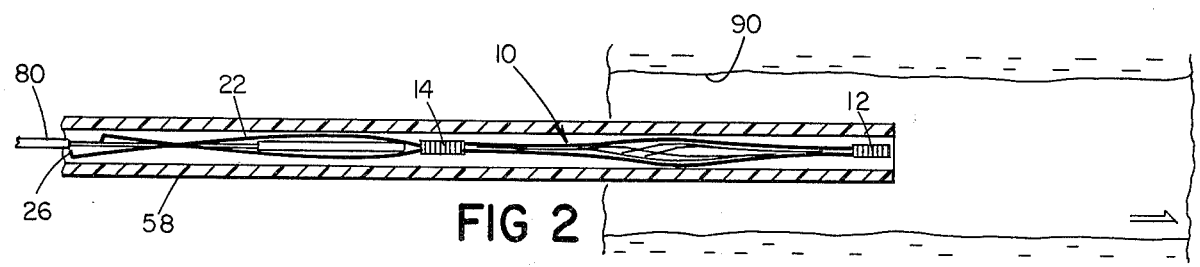
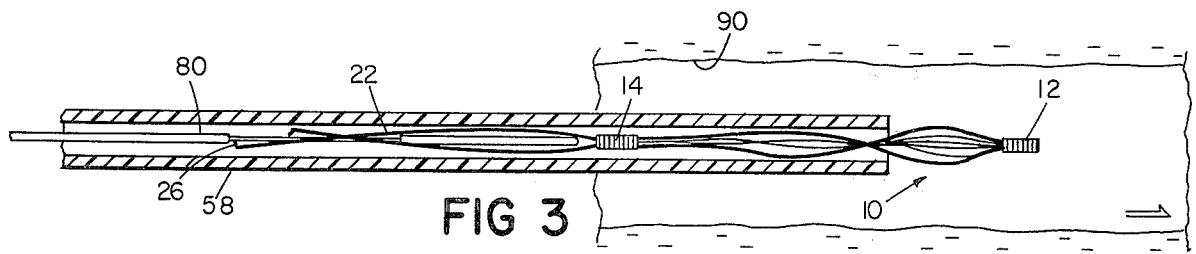
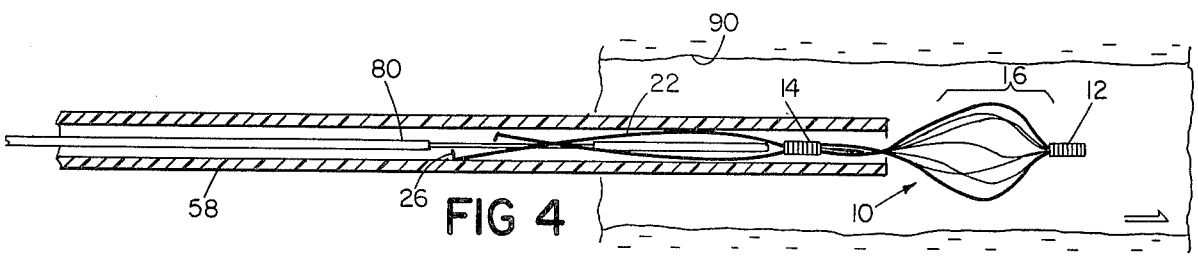

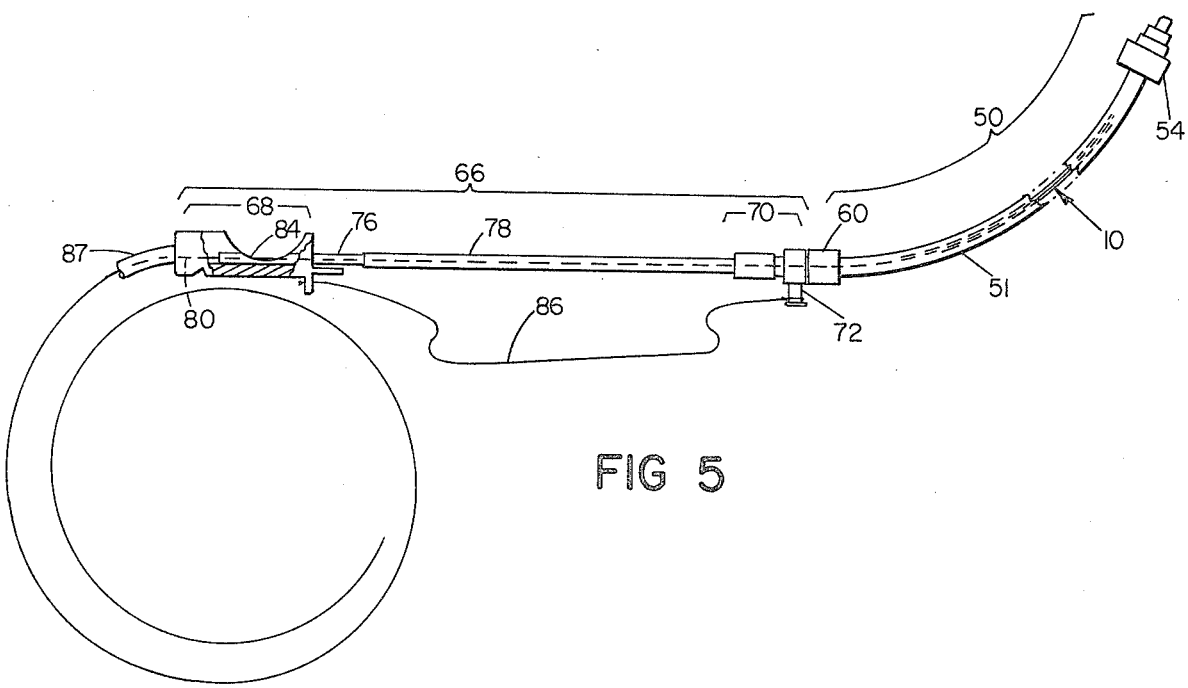
FIG 5
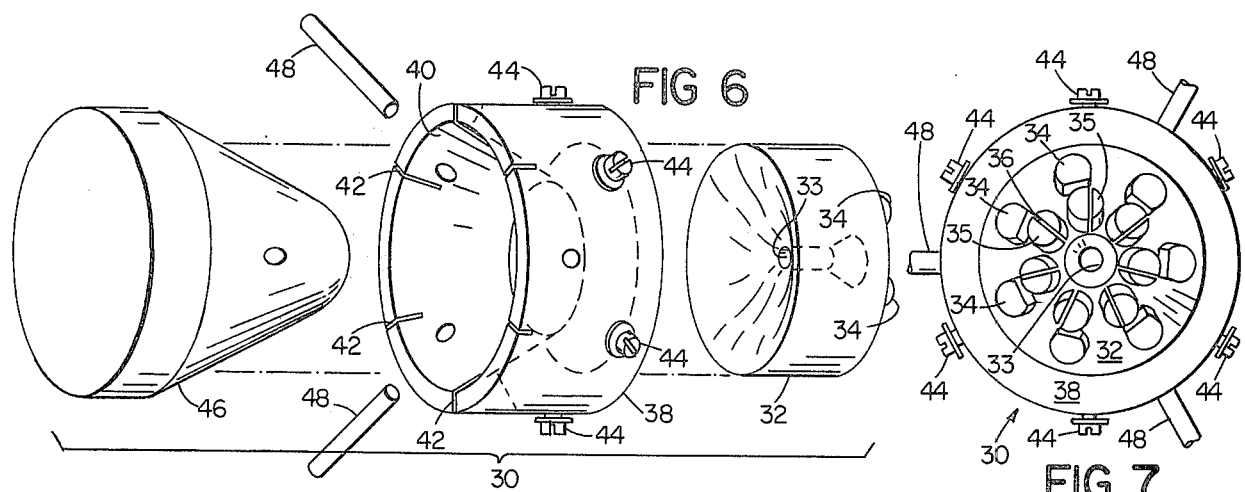
FIG 6
FIG 7
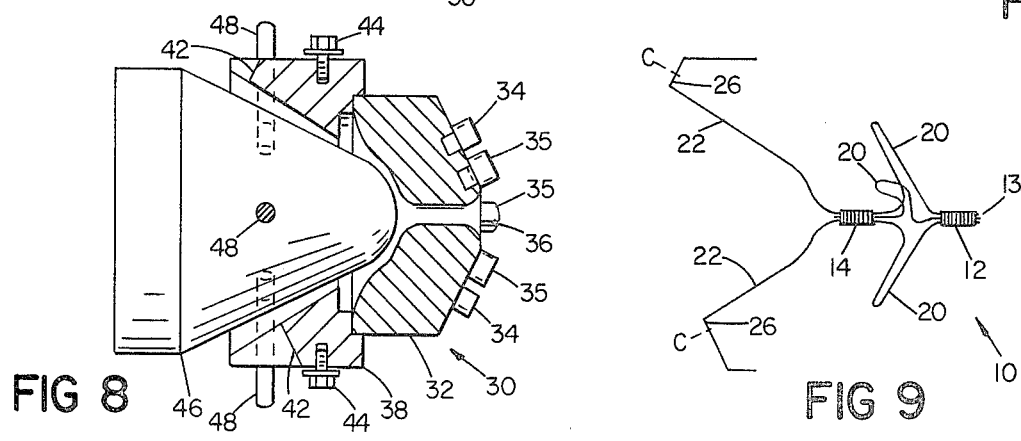
FIG 8
FIG 9

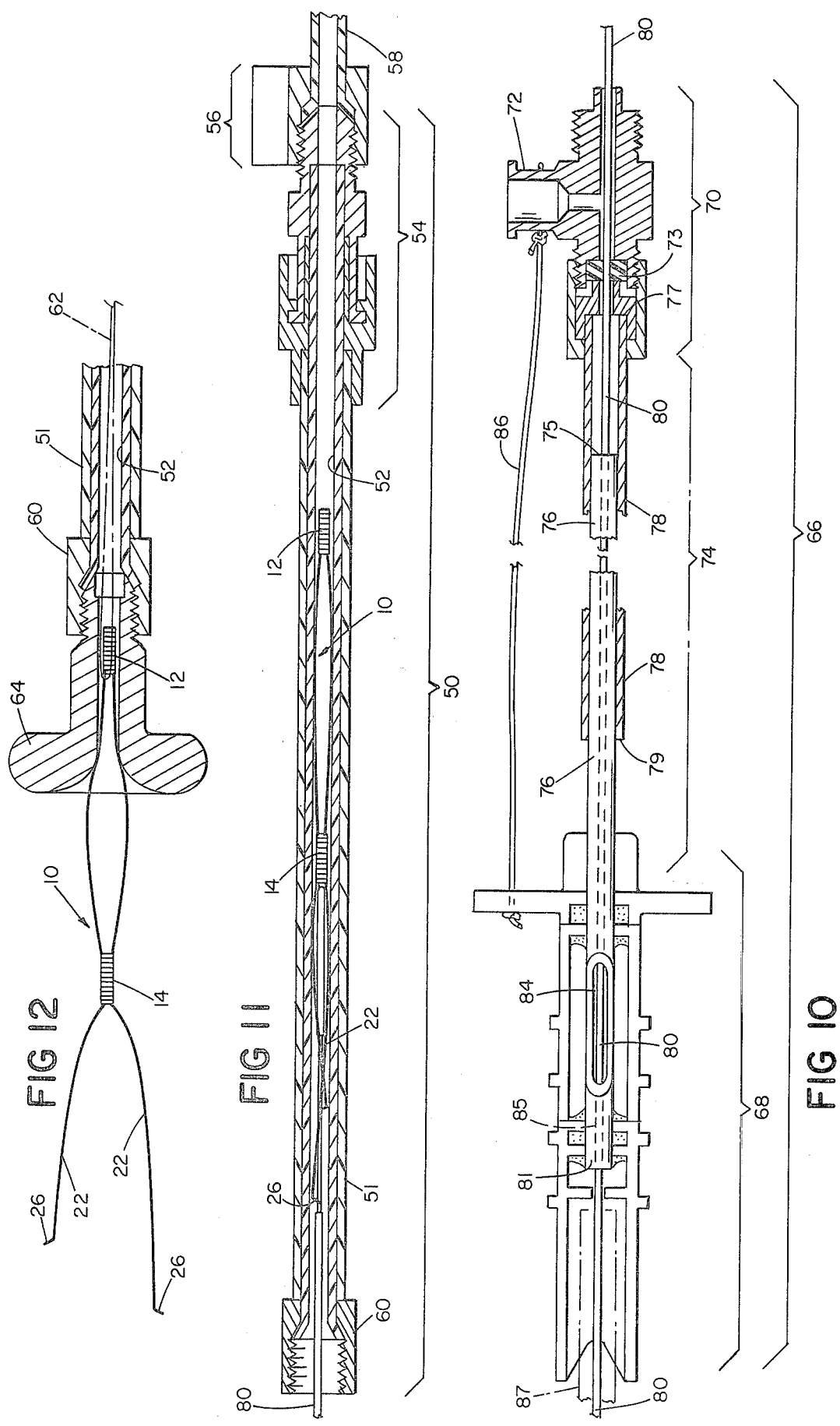

BLOOD CLOT FILTER

This invention relates to blood clot filters and devices for inserting filters into patients.

BACKGROUND OF THE INVENTION

When a blood clot that has formed in a vein of the lower part of the body breaks loose and migrates to the lungs, pulmonary embolism results. These clots obstruct the flow of blood through the lungs and interfere with the normal oxygenation of the blood. Whereas small clots may be tolerated and eventually reabsorbed, large clots (greater than three millimeters in diameter and up to 30 centimeters in length) can cause shock or sudden death. Pulmonary embolism causes approximately 200,000 deaths in the U.S.A. each year.

Pulmonary embolism has a tendency to recur. If a patient has had one pulmonary embolism, there is a probability of about 70% that he will have another. If the patient survives the initial embolism, treatment is usually directed toward preventing further blood clot formation in the veins (anticoagulation). However, some patients cannot be given anticoagulants, for example after injury, surgery or stroke, and others may have recurrent embolism despite anticoagulant treatment. Further, anticoagulants do not affect clots already formed.

As an alternative to anticoagulants, the travelling clots (emboli) may be prevented from reaching the lungs by interrupting their passage through the inferior vena cava, the great vein which returns blood from the lower half of the body to the heart and lungs. Traditionally this has been done by direct surgery on the vena cava; the vena cava has been simply tied (ligated), or its cross-section has been subdivided by a variety of sutures or clips. More recently the vena cava has been interrupted by inserting into the vena cava a filtering or obstructing device indirectly via a remote but more accessible vein, such as the jugular vein in the neck or the femoral vein in the groin.

There are known in the prior art several devices to interrupt the travel of emboli. All of these devices require surgical dissection of the vein of entry for their insertion.

First, the Miles or Adams-DeWeese plastic clip may be used to flatten and subdivide the lumen of the vena cava from the outside. This is very effective in interrupting the travel of emboli. However, this device requires major abdominal surgery, sometimes on very sick patients. There may be complications of the abdominal surgery or the general anesthesia even though the clip itself is effective and is not subject to local complications such as bleeding, perforation or migration.

Alternatively, several prior art transvenous devices are known. The most popular devices are the Mobin-Uddin umbrella, the Kimray-Greenfield filter, and the Hunter balloon.

All three require surgical dissection of the internal jugular vein in the neck or the femoral vein in the groin, usually under local anesthesia. The vein must be opened to insert the capsule containing the folded device or the collapsed Hunter balloon. This dissection may take half an hour to three hours before the folded device or collapsed balloon can be inserted into the large vein. The procedure is very uncomfortable for the patient who must lie still during the dissection.

The dissection is usually done by a surgical team consisting of a surgeon, an assistant and an operating room nurse in addition to the radiologist and radiologic technologist. A delay of some hours is usually required to mobilize this team. The radiologist generally prechecks the anatomy of the vena cava fluoroscopically by injecting contrast agent through a catheter positioned near its lower end. He guides the device into optimal position for delivery. The umbrella, filter or inflated balloon is released into the vena cava. The radiologist may inject contrast medium after delivery in order to check for position and/or patency of the device.

Dissection of the vein is associated with a risk of local hemorrhage and a further risk of air embolism through the vein incision. Further, the device may be difficult or impossible to insert, and it may prove difficult to steer the device into its correct position. The insertion process is thus complex, time consuming, expensive and sometimes associated with surgical complications at the site of introduction. Generally the large vein in the neck or groin is sacrificed after removing the delivery system.

In addition there are problems associated with specific devices.

The Mobin-Uddin umbrella (described in U.S. Pat. No. 3,540,431, issued Nov. 17, 1970) may be dislodged and migrate toward the heart and lungs. The device tends to become totally obstructed by even small amounts of embolus. Elevated venous pressure occurs below the umbrella, and this may cause leg edema. Thrombosis may occur in the cul-de-sac above the umbrella and this can be a source of recurrent pulmonary emboli. Finally, perforation of the vena cava wall with local hemorrhage may occur.

The Kimray-Greenfield filter is described in U.S. Pat. No. 3,952,747, issued Apr. 27, 1976. Using the Kimray-Greenfield filter, there may be difficulty inserting the capsule, which is relatively large. The device tends to tilt backward or sideways during or after delivery, becoming mechanically less effective. The device may migrate distally due to the waterhammer effect of the column of blood above the filter. Perforation of the vena cava may occur, sometimes with local hemorrhage. Moderate sized emboli may pass through the filter, particularly if it is tilted or the vena cava is large. However, proximal migration of the Kimray-Greenfield filter has not been reported, and the device generally remains clot free.

The Hunter balloon device is designed to completely occlude the lumen of the vena cava, and thus may cause leg edema. Large collateral veins open up and these may also allow passage of dangerous emboli. This device is also expensive. However, the Hunter balloon has the advantage that it can be repositioned, if necessary, before release. It is not associated with perforation or local hemorrhage and migration is rare.

In view of the problems with these prior art devices, it would be desirable to provide a device for preventing pulmonary embolism that can be inserted into the vena cava without surgical dissection of a vein of entry. It is further desirable to provide such a device that can be inserted immediately upon diagnosis of the need for the device, at the time of the diagnostic procedure, without calling upon a surgical team.

It is also desirable to provide such a device that is easy to insert, takes very little time to insert, and is associated with minimal risk of surgical complications such as local hemorrhage or air embolism.

It is further desirable to provide means for inserting the device which is easy to use and is adapted for use with existing apparatus used during the diagnostic procedure.

It is therefore an object of the invention to provide a filter for interrupting the travel of emboli that can be inserted by the radiologist at the time of diagnosis, without requiring the presence of a surgical team.

It is also an object of the invention to provide such a filter that can be firmly attached to the vein, that is not easily dislodged, that does not tend to become totally obstructed by retained emboli, that does not tend to cause thrombosis, leg edema or other complications, and that retains all potentially dangerous emboli.

It is an additional object of the invention to provide means for inserting such a filter into the patient that is easy to use, and is adaptable for use with standard angiographic catheters used during diagnostic procedures.

Commonly, for procedures involving placement of a catheter in a blood vessel of a patient, a needle is first inserted in the blood vessel; a guide wire is then threaded through the needle; the needle is then withdrawn over the guide wire; and finally the catheter (tubing) is inserted into the vessel over the guide wire. This method is known as the Seldinger technique. The insertion of the guide wire requires skill, and a problem ofter occurs when the wire meets resistance and buckles (outside the patient), after which the wire cannot be used and must be withdrawn, and another wire started. It would be desirable to provide a guide wire feed device which will prevent this problem. The device according to the present invention can be used to deliver any guide wire. In particular, it is used to deliver a guide wire which in turn delivers the filter of the invention through the catheter, as described herein.

BRIEF DESCRIPTION OF THE INVENTION

According to the invention, a resilient, longitudinally extended blood clot filter is inwardly radially collapsible toward its longitudinal axis into a collapsed configuration for insertion into a vein, for automatic radial expansion into contact with the inner wall of the vein at two longitudinally spaced peripheral locations therein. The filter has leading and trailing ends and comprises a plurality of wires. The wires, in the normal expanded configuration of the filter, are in the form of a plurality of overlapping loops with openings between the wires providing a filter basket at the leading end of the filter, and have peripheral portions for contact of the wires with the inner wall of the vein at one peripheral location. At the trailing end of the filter the wires are in the form of circumferentially spaced leg portions having free ends, for contact with the inner wall of the vein at another peripheral location longitudinally spaced from the first.

To provide a filter that is inwardly radially collapsible from its normally expanded configuration toward its longitudinal axis into a collapsed configuration for insertion into a vein, the blood clot filter comprises a plurality of wire portions composed of a material having a first, low-temperature condition and a second, high-temperature condition. The material in its low-temperature condition is relatively pliable (so that the wire portions may be straightened) and in its high-temperature condition is resiliently deformable and relatively rigid, and takes a pre-determined functional form.

In both conditions of the material, the filter has a longitudinal axis and a leading end located on the axis; the wire portions are confined together at the filter leading end to form a tip, and are also confined together at a median place on the axis spaced from the leading end. The wire portions have free ends remote from the tip and the median place; the wire portions between the median place and free ends define legs.

In the high-temperature condition of the material, the filter comprises coaxial first and second filter baskets, each filter basket being generally symmetrical about the longitudinal axis and convex relative to the filter leading end.

In preferred embodiments, in the high-temperature condition of the material, each wire portion between the filter tip and the median place forms a loop; each loop overlaps at least the adjacent two loops, and the loops form the first filter basket. Each wire portion leg is bowed outwardly from the median place and provides a foot bent at an angle at the free end; the wire portion legs form the second filter basket. One wire portion extends only from the filter tip to the median place and terminates thereat to provide a thrust-bearing surface. Preferably, the wire portion legs are of unequal lengths.

A filter according to the invention has several advantages. In particular, there is no necessary delay between the decision to insert the filter device and its actual insertion. Because the device is inserted by passing it through a fine bore flexible plastic catheter which is introduced into the vein by a simple needle puncture technique, surgical dissection is eliminated entirely. The actual delivery of the device is quick and easy under fluoroscopic control once the catheter is in position. It takes less than 30 seconds to accomplish. The filtration is highly effective for relatively small emboli. It is anticipated that the complication rate will be very low. As a result of these advantages, it is anticipated that the indications for placement of a filter will be broadened, and that the filter can be used more widely than has been the case with prior art filters.

In another aspect of the invention, a guide wire feeder device suitable for introducing the filter into the blood vessel of a patient comprises a handle portion, and first and second tubular sections. The tubular sections are adapted to permit motion of a guide wire through them. The handle portion is attached to a first tubular section to define a unit movable relative to the second tubular section. One tubular section is smoothly slidable within the other tubular section for longitudinal extension and contraction of the guide wire feed device. Extension limiting means is connected between the unit and the second tubular section, and defines a furthest extension of the unit with respect to the second tubular section.

The handle portion provides a passage communicating with the interior of the tubular sections and adapted to permit motion of a guide wire through the passage and the tubular sections. The handle portion further provides feed means adjacent the passage permitting releasably fixing the longitudinal position of the guide wire with respect to the unit. Thus, the guide wire can be advanced when the feed device is contracted, by fixing the position of the guide wire with respect to the unit and advancing the unit with respect to the second tubular section; when the unit is retracted with respect to the second tubular section, the guide wire is released and therefore is not retracted with the unit.

Other objects, features, and advantages will be apparent from the following description, together with the drawing, in which:

FIG. 1 shows the filter of the invention in place in a vein;

FIGS. 2, 3, 4 and 13 show the filter at four stages during its placement in the vein;

FIG. 5 shows filter and filter delivery device before insertion of the filter into the vein;

FIG. 6 shows an exploded view of the forming means for the filter;

FIG. 7 is an end view of a portion of the forming means;

FIG. 8 shows the forming means assembled, in partial section;

FIG. 9 shows portions of the filter as positioned in the forming means of FIG. 8;

FIG. 10 shows a first (guide wire feeder) portion of the filter delivery device;

FIG. 11 shows a further (filter storage) portion of the filter delivery device, with filter in place therein; and FIG. 12 shows the filter being loaded in the filter storage portion.

DETAILED DESCRIPTION

To provide the filter of the invention, which is radially collapsible for insertion through a catheter, the filter in a preferred embodiment is composed of a material that is relatively soft and pliable at a temperature below about 70° F., and that assumes and retains a predetermined shape at a temperature above about 90° F. In its high-temperature condition, the material is relatively stiff.

The filter of this embodiment is composed of fine wires, having a preformed high-temperature shape to be described. In its low-temperature state, the filter can be straightened and passed through a small-bore plastic tube (or catheter) previously positioned in the vena cava by simple needle puncture of a vein in the groin, neck or limbs (the Seldinger technique). The wire filter is kept cool and pliable by flowing cold saline solution around it while it is being advanced through the catheter under x-ray fluoroscopic control. As the filter is extruded from the catheter into the vena cava the device is exposed to body temperature and becomes progressively transformed into its filter shape quickly and automatically, as will be described.

A suitable material for the filter, which is used in the preferred embodiment, is generally known, and is referred to as "Nitinol". This material is an alloy of nickel and titanium, and was initially developed in the U.S. Naval Ordnance Laboratory for the possible construction of an antenna for use in space; the antenna could be compressed during the launch of the satellite, but upon exposure to sunlight, would expand to a predetermined, functional shape having a large area. The material is more particularly described in the publication "55-Nitinol—The alloy with a Memory: Its Physical Metallurgy, Properties, and Applications, A Report" by C. M. Jackson, H. J. Wagner, and R. J. Wasilewski, NASA-SP 5110, Technology Utilization Office, National Aeronautics and Space Administration (1972).

Nitinol is very inert; it is less reactive than stainless steel. Therefore a filter made of Nitinol is not likely to cause adverse reactions within the body.

Nitinol exists in a number of particular forms, responsive to different temperature thresholds. The particular alloy which has the temperature characteristics needed for the filter of the invention is 55.1 weight percent nickel with the balance titanium.

In the preferred embodiment, the Nitinol wire is approximately 13/1000 of an inch in diameter. The low temperature phase exists below 70° F. At this temperature the material is relatively soft and pliable. The high temperature phase exists above 90° F. At this temperature the material is relatively rigid and assumes a predetermined shape.

Referring now to the drawing, and particularly to FIG. 1, the filter 10 is made up of a set of seven Nitinol wires. Six of these are approximately three inches in length when fully extended. The seventh is approximately two inches in length when fully extended. (The purpose of the shorter wire will be explained.) The wires are held together by two small sleeves or coils 12 and 14 of the same material, each coil being spot welded to hold it in place and approximately one-quarter of an inch in length; coil 12 is adjacent the tip 13 of the seven wires, and coil 14 is approximately two inches from tip 13 when the wires are fully extended (FIG. 2). In the low temperature phase of the material (FIG. 2) the set of wires can be straightened and held in a straight form that can pass through a length of fine plastic tubing with an internal diameter of approximately 2 mm (#8 French catheter). In its high temperature form (FIG. 1) filter 10 recovers a preformed filtering shape.

According to the invention, in its normal expanded configuration or performed filtering shape, filter 10 is a double filter, having a first filter basket 16 and a second filter basket 18. The two filter baskets provide peripheral portions which engage the inner wall of the vein at two longitudinally spaced locations. The two filter baskets are generally symmetrical about a longitudinal axis passing through filter tip 13.

The mesh of first filter basket 16 is formed from the sections of wires between the two quarter-inch coils 12 and 14. The mesh is made up of a series of seven overlapping loops 20 arranged to form a rosette approximately 25 mm in diameter. The loops are angled slightly relative to the long axis of filter 10 and this angle can be varied to accommodate somewhat smaller diameters if the device is to be constrained in a tube of less than 25 mm in caliber. The loops 20 effectively divide the cross-sectional area to be filtered. The rosette formed by loops 20 can expand or be compressed to fit various sizes of vein. The peripheral portions or tips of the loops 20 press outwardly against the inner wall of the vein, although without becoming imbedded in the vein; loops 20 thereby help to keep filter 10 in place. (The presence of the filer is not felt since the lining of the vein is insensitive.) First filter basket 16 is convex relative to filter tip 13.

The mesh of second filter basket 18 is formed by the six circumferentially spaced free wire ends or legs 22, which tilt and bow outwardly of the long axis of filter 10. (The seventh wire terminates within sleeve 14 for use in inserting filter 20, as will be described.) The six free ends or legs 22 that extend beyond the second quarter inch coil 14 diverge so that their tips form a circle 24 of approximately 40 mm in diameter at their maximum divergence. Each leg is also bowed outwardly slightly. The legs serve to orient the device relative to the long axis of the vena cava. Second filter basket 18 is convex relative to filter tip 13.

In an alternative embodiment (not shown) the legs are tilted outwardly but are not formed with a bow. In such an embodiment, second filter basket 18 opens away from filter tip 13 without being strictly convex.

Each free end of leg 22 is bent sharply outward at about a right angle to form a hook 26 of approximately 1.5 mm in length. The hooks are intended to engage the wall of the vena cava to prevent migration proximally or distally.

The six legs 22 are of slightly different lengths to permit good packing within the delivery device, as will be described; if legs 22 are all of a single length, the hooks may interfere with one another, so that the filter does not expand properly when delivered into the vein.

Referring now to FIGS. 6, 7, 8 and 9, a jig 30 is employed to restrain the set of wires in the predetermined filter form during the process of annealing it in a furnace. This is the forming means used to imprint the "memory" of the high temperature form on the filter device.

Jig 30 has three parts. The first part is a mushroom-like cap 32 with a 2 mm central hole 33 through which the set of wires is passed. Two sets of pegs are provided on the outer surface of cap 32. The first is the outer set of pegs 34; the second is the inner set of pegs 35, which provide slits 36. The wires of the filter are draped over the outer surface of cap 32, through slits 36 and around pegs 34 and 35, to form the seven overlapping loops of the first filter basket.

The second part of jig 30 is a sleeve 38 which fits against the base of cap 32. The jig parts 38 and 32 could be made as a single piece. The inner surface of sleeve 38 defines a conical central cavity 40 which allows the filter legs to be spread evenly. Sleeve 38 further has shallow grooves 42 cut into it to receive the wires of the filter and to form in them the sharply angled hooks 26. The grooves 42 are of varying depths, which define the varying lengths of the filter legs. Sleeve 38 provides six holding screws 44 to restrain the material during annealing.

The third part of jig 30 is a bulging cone element 46 that fits into conical cavity 40 of sleeve 38 to produce slight outward bowing of each of the legs during annealing of the filter.

A set of seven wires is wrapped around pegs 34 and 35 of cap 32. The forward ends of the wires are confined in sleeve 12. The rearward ends of the wires are drawn through central hole 33 of cap 32 and confined in sleeve 14. Cap 32 is set into sleeve 38. The free ends of the wires are drawn back through central cavity 40 of sleeve 38 and through the slits 42, and are fastened by screws 44. The tension on the wires holds pieces 32 and 38 of jig 30 together. Cone element 46 is placed within central cavity 40 of sleeve 38, and held in place by three pins 48.

Jig 30 is loaded with the set of wires in an environment having a temperature below 60° F. The jig and restrained wires are then annealed in a furnace at approximately 1020° F. for approximately twenty minutes. The filter wires take on the shape shown in FIG. 9 (certain of the seven wires have been omitted for clarity). The assembly is then allowed to cool to room temperature so that the wires become pliable once again for unloading. The filter is then removed from the jig and warmed to about 98° F. to restore its high temperature shape. Cuts are made at the places indicated by C. The filter can now be straightened for storage in the delivery system.

For use, the filter is provided in combination with a filter delivery device (FIG. 5) designed to be used with a standard catheter already in place in the patient. The delivery device comprises generally a filter storage tube 50 and a guide wire feeder 66, which provides a cool drip infusion element 72.

In general, in any procedure involving placement of a catheter in a blood vessel of a patient, a needle is first inserted in the blood vessel; a guide wire is then threaded through the needle; the needle is then withdrawn over the guide wire; and finally the catheter (tubing) is inserted into the vessel over the guide wire. The insertion of the guide wire requires skill, and a problem often occurs when the wire meets resistance and buckles (outside the patient), after which the wire cannot be used and must be withdrawn, and another wire started. The guide wire feeder described herein will prevent this problem. This guide wire feeder can be used to deliver any guide wire. In particular, it is used to deliver a guide wire which inserts the filter of the invention, as described herein.

To implant the filter requires the use of the following parts which connect together: a delivery device, which comprises a filter storage tube and a guide wire feeder including a cool drip infusion element, and a catheter.

Referring now to FIG. 11, the filter storage tube 50 is a 4" section of thick-walled transparent plastic tubing 51 with a lumen 52 of about 2 mm. At one end there is a standard luer-lock adapter 54 to attach to the fitting 56 of a catheter 58 previously inserted in the patient. At the other end of tube 50 there is a fitting 60 suitable to be connected with the guide wire feeder, to be described.

In its low-temperature state, filter 10 is straightened and can be drawn into storage tube 50 with the aid of a thin wire loop 62 (FIG. 12). During the last part of the loading process the legs 22 of filter 10 are spread over a loading "donut" 64 to ensure perfect alignment of the legs as they are drawn into storage tube 50.

Referring now to FIG. 10, guide wire feeder 66 attaches to adapter 60 at the rear end of storage tube 50. Feeder 66 comprises a handle portion 68 remote from storage tube 50, a standard two-way adapter 70 for connection to storage tube 50, and a variable length portion 74 therebetween. Adapter 70 provides a standard rubber seal connection (Touhy-Borst) and a side arm 72 to receive an infusion of fluid. The rubber seal 73 prevents reflux of the infusion fluid, and also provides some resistance to prevent accidental withdrawal of the guide wire.

The variable length portion 74 of guide wire feeder 66 comprises two sections of metal tubing, each about 3 inches in length; a first section 76 has a smaller diameter than the other section 78 so as to slide snugly within it. Smaller tube 76 has an inner diameter of about 1.5 mm to permit a long coil spring guide wire 80 of about 50/1000 of an inch to pass through it. The forward end 75 of inner tube 76 is free. The forward end 77 of outer tube 78 is attached to adapter 70, while its rear end 79 is free.

The rear end 81 of inner metal tube 76 is attached to handle 68 to define a unit, movable relative to outer tube 78. Handle 68 provides a passage 85 for guide wire 80, communicating with the interior of tubes 76 and 78, adapted to permit motion of guide wire 80 through the passage and tubes. In the particular embodiment described herein, a portion of the passage is provided by an extension of tube 76. Handle 68 and inner tube 76 provide an elongated aperture 84 about ¾" in length, adjacent passage 85, opening around approximately two-thirds of the circumference of guide wire 80, to permit thumb pressure to be exerted on the guide wire. Aperture 84 provides feed means permitting releasably fixing the longitudinal position of the guide wire with respect to the unit. The handle is also connected with a loop of plastic tubing 87 (FIG. 5) which houses the coiled guide wire, keeping it sterile.

By means of handle 68, the user advances and retracts inner tube 76 with respect to outer tube 78. Advance of inner tube 76 is limited when the free end 79 of outer tube 78 engages handle 68. Retraction of inner tube 76 (and extension of the feed device) is limited by a 5" nylon thread 86 which connects handle 68 of feeder 66 to two-way adapter 70. Guide wire 80 thus passes from the protective loop 86 of plastic tubing through handle 68, through the pair of metal tubes 76 and 78, through two-way adapter 70 and its rubber seal and into the filter storage tube 50. The tip of guide wire 80 butts up against the thrust-bearing surface provided by the short seventh wire of filter 10 at the center of the proximal coil sleeve 14 which holds the set of filter wires together.

In use, feeder 66 is first extended; tubes 76 and 78 are separated as far as permitted by thread 86; the user's thumb is then pressed against guide wire 80 within aperture 84, and filter 10 is pushed forward approximately 4" by closing tubes 76 and 78 of feeder 66. The thumb is then released, feeder 66 is again extended, thumb pressure is reapplied and filter 10 is advanced another 4" by closing the feeder. This process is repeated to advance the filter along the length of catheter 58 and to extrude it into the vena cava.

Catheter 58, which has been introduced into the blood vessel of the patient, is a section of fine plastic tubing of approximately 2 mm internal diameter (#8 French catheter). It is about 60 cm in length and its tip is not tapered. At the proximal end of catheter 58 there is a fitting 56 suitable to be attached to the standard luer-lock adapter 54 of storage tube 51. The attachment is such that the lumen of the storage tube is continuous with and matches in caliber the lumen of the catheter. Before attachment of the filter delivery device, a stopcock (not shown) may be inserted in the fitting, to prevent bleeding through the catheter and to allow infusion of intravenous fluid.

Catheter 58 has been previously introduced into the venous system of the patient by a standard percutaneous needle puncture technique (the Seldinger technique). In this process the vein is punctured by a needle, a guide wire is passed through the lumen of the needle, the needle is removed leaving the guide wire in place, a catheter is passed over the guide wire into the lumen and finally the guide wire is removed leaving the catheter 58 in the vein. The X-ray dye (contrast medium) used in the diagnostic procedure is introduced through the catheter. Under fluoroscopic guidance the tip of the catheter is guided into the vena cava and positioned at the site judged to be optimal for delivery of the filter.

A plastic infusion bag of normal saline solution (not shown) is kept at a temperature between 40°-50° F. in a refrigerator. This bag is now connected through standard tubing (not shown) to infusion element 72 of two-way adapter 70 at the proximal end of storage tube 50. The cooled liquid is allowed to infuse through storage tube 50 and around filter 10 at a steady rate controlled by an adjustable drip control device (not shown) on the tubing.

Guide wire feeder 66, filter storage tube 50 connected to it, filter 10 collapsed within storage tube 50, and guide wire 80 with its tip butting the collapsed filter and its length wound within its sterile storage coil 86, are prepared as a unit, and kept refrigerated until wanted. After use, the wire feeder 66 and storage tube 50 are disposed of.

Insertion of the Filter

After the diagnostic procedure has been completed and a decision has been made to insert the filter, the stopcock (not shown) is removed from catheter adapter 56.

With the cold infusion drip running, storage tube 50 (to which guide wire feeder assembly 66 is attached) is connected to catheter 58 already positioned in the patient. Guide wire 80 butts against the short seventh wire of filter 10, at the end of sleeve 14. Referring now to FIGS. 2, 3 and 4, guide wire feeder 66 is then operated to push the pliable straight filter 10 (in its low temperature state) out of storage tube 50, along catheter 58 and into vena cava 90. In the vena cava filter 10 is exposed to body temperature for the first time and as each portion of filter 10 is warmed to body temperature, it is immediately transformed into its high temperature phase.

Once delivered, as seen in FIG. 1, filter 10 is designed to lock into place by the outward pressure of loops 20 against the inner wall of vena cava 90, as well as by the engagement of hooks 26 with the inner wall. This action locks filter 10 into position in the vena cava, where it can function as an effective trap for emboli coming from the lower part of the body. The delivery process should take less than 30 seconds, if catheter 58 is already positioned in the vena cava.

Once filter 10 is delivered, guide wire feeder 66, storage tube 50 and catheter 58 are immediately withdrawn, and gentle pressure is applied over the needle puncture site to permit its natural sealing. Filter 10 is now positioned in the vena cava and functions as a trap for emboli from the lower part of the patient's body. The device serves as a permanent and effective blood clot filter, allowing normal blood flow through its interstices but trapping dangerous embolising blood clots.

The principal advantage of the filter of the invention is that it is deliverable through a standard angiographic catheter, which in practice has already been put in place by simple needle puncture of a remote vein for the diagnosis of pulmonary embolism. Therefore delivery of the filter is a non surgical procedure, that can be done by the same physician who is doing the angiography. The process takes less than 30 seconds, as contrasted with several hours for the assembly of a surgical team and the surgical dissection procedure required to insert the prior art filters.

Various modifications of the invention, within the spirit thereof and the scope of the appended claims, will occur to those skilled in the art.

What is claimed is:

1. A blood clot filter comprising a plurality of wire portions composed of material having a first, low-temperature condition and a second, high-temperature condition, said material in its low-temperature condition being relatively pliable and in its high-temperature condition being resiliently deformable and relatively rigid and taking a pre-determined functional form, said material having its high-temperature condition at about body temperature, in both material conditions, said filter having a longitudinal axis and a leading end located on said axis, said wire portions being confined together at said filter leading end to form a tip, said wire portions being confined together at a median place on said axis spaced from said filter leading and, said wire portions having free ends remote from said tip and said median place, said wire portions between said median place and said free ends defining legs, in said material high-temperature condition, said filter comprising coaxial first and second filter baskets, each said filter basket being generally symmetrical about said longitudinal axis and opening away from said filter leading end.

2. The filter of claim 1, wherein in said material high-temperature condition, each said wire portion between said filter tip and said median place forms a loop, a said loop overlapping at least the adjacent two said loops, said loops forming said first filter basket.

3. The filter of claim 1, wherein in said material high-temperature condition, each said wire portion leg is bowed outwardly from said median place and provides a foot bent at an angle at said free end, said wire portion legs forming said second filter basket.

4. The filter of claim 1, one said wire portion extending only from said filter tip to said median place and terminating thereat to provide a thrust-bearing surface.

5. The filter of claim 4, said wire portion legs being of unequal lengths.

6. A blood clot filter comprising a plurality of wire portions having first and second ends and composed of material having a first, low-temperature condition and a second, high-temperature condition, said material in its low-temperature condition being relatively pliable and in its high-temperature condition being resiliently deformable and relatively rigid and taking a pre-determined functional form, said material having its high-temperature condition at about body temperature, in both material conditions, said filter having a longitudinal axis and a leading end located on said axis, said wire portion first ends being confined together at said filter leading end to form a tip, said wire portions being further confined together at a median place on said axis spaced from said filter leading end, said wire portion second ends being free, said wire portions between said median place and said free second ends defining legs, in said material high-temperature condition, said filter comprising coaxial first and second filter baskets, each said filter basket being generally symmetrical about said longitudinal axis and convex relative to said filter leading end, each said wire portion between said filter tip and said median place forms a partial loop, a said partial loop overlapping at least the adjacent two said partial loops, said partial loops forming said first filter basket, each said wire portion leg being bowed outwardly from said median place and providing a foot bent at an acute angle at said free end, said wire portion legs forming said second filter basket, said wire portion legs being of unequal lengths, one said wire portion extending only from said filter tip to said median place and terminating thereat to provide a thrust-bearing surface.

7. A resilient, longitudinally extended, blood clot filter
inwardly radially collapsible from its normally expanded configuration toward its longitudinal axis into a collapsed configuration for insertion into a vein for automatic radial expansion into contact with the inner wall of said vein at two longitudinally spaced peripheral locations therein, said blood clot filter having leading and trailing ends and comprising a plurality of wires, said wires, in the normal expanded configuration of said filter, being in the form of a plurality of overlapping loops with openings between said wires providing a filter basket at the leading end of said filter and having peripheral portions for contact of said wires with the inner wall of said vein at one of said longitudinally spaced locations and at the trailing end of said filter being in the form of circumferentially spaced leg portions having free ends for contact with the inner wall of said vein at the other of said longitudinally spaced locations to provide a blood clot filter secured to the vein wall for collecting blood clots passing through said vein.

8. For use in introducing a guide wire into a blood vessel, and advancing it therethrough, a guide blood vessel catheter guide wire delivery apparatus for advancing a catheter guide wire within a blood vessel without buckling externally of the blood vessel, said apparatus comprising a handle portion first and second tubular sections, adapted to permit motion of a guide wire therethrough, said handle portion being attached to a first said tubular section to define a unit movable relative to the second said tubular section, one said tubular section being smoothly slidable within the other said tubular section for longitudinal extension and contraction of said guide wire feed device, extension limiting means connected between said unit and said second tubular section and defining a furthest extension of said unit with respect to said second tubular section, said handle portion providing a passage communicating with the interior of said tubular sections and adapted to permit motion of a guide wire through said passage and said tubular sections, said handle portion further providing feed means adjacent said passage permitting releasably fixing the longitudinal position of the guide wire with respect to said unit, and permitting the application of forward force to the guide wire at a point within said feed device, whereby said guide wire can move an implantable blood clot filter or the like to a desired location within the blood vessel.

9. In combination, a blood clot filter and a filter delivery device, said filter delivery device comprising a filter storage tube, a guide wire, and a guide wire feed device, said filter comprising a plurality of wire portions composed of material having a first, low-temperature condition and a second, high-temperature condition, said material in its low-temperature condition being relatively pliable and in its high-temperature condition being resiliently deformable and relatively rigid and taking a pre-determined functional form, in both material conditions, said filter having a longitudinal axis and a leading end located on said axis, said wire portions being confined together at said filter leading end to form a tip, said wire portions being confined together at a median place on said axis spaced from said filter leading end, said wire portions having free ends remote from said tip and said median place, said wire portions between said median place and said free ends defining legs, in said material high-temperature condition, said filter comprising coaxial first and second filter baskets, each said filter basket being generally symmetrical about said longitudinal axis and opening away from said filter leading end, said guide wire feed device comprising first and second tubular sections, adapted to permit motion of said guide wire therethrough, said handle portion being attached to a first said tubular section to define a unit movable relative to the second said tubular section, one said tubular section being smoothly slidable within the other said tubular section for longitudinal extension and contraction of said guide wire feed device, extension limiting means connected between said unit and said second tubular section and defining a furthest extension of said unit with respect to said second tubular section, said handle portion providing a passage communicating with the interior of said tubular sections and adapted to permit motion of said guide wire through said passage and said tubular sections, said handle portion further providing means adjacent said passage, for releasably fixing the longitudinal position of said guide wire with respect to said unit, and permitting the application of forward force to said guide wire at a point within said feed device, a first end of said filter storage tube being attached to the end of said feed device second tubular section remote from said feed device handle, the second end of said filter storage tube being adapted for attachment to a catheter, said filter in its low-temperature condition being within said filter storage tube, and said guide wire being engageable with said filter for motion thereof away from said feed device and out of said storage tube.

* * * * *